United States Patent
Ales et al.

(10) Patent No.: US 8,642,832 B2
(45) Date of Patent: Feb. 4, 2014

(54) APPARATUS AND METHOD FOR PRODUCT AND SIGNALING DEVICE MATCHING

(75) Inventors: Thomas Michael Ales, Neenah, WI (US); Sudhanshu Gakhar, Neenah, WI (US); Andrew Mark Long, Appleton, WI (US); Davis-Dang H Nhan, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 467 days.

(21) Appl. No.: 12/943,602

(22) Filed: Nov. 10, 2010

(65) Prior Publication Data

US 2012/0116337 A1    May 10, 2012

(51) Int. Cl.
*A61F 13/42* (2006.01)

(52) U.S. Cl.
USPC .......................................................... 604/361

(58) Field of Classification Search
USPC .............................. 604/361, 362, 367, 385.01
See application file for complete search history.

(56) References Cited

U.S. PATENT DOCUMENTS

| | | | |
|---|---|---|---|
| 4,704,116 A | 11/1987 | Enloe | |
| 4,800,370 A | 1/1989 | Vetecnik | |
| 4,940,464 A | 7/1990 | Van Gompel et al. | |
| 5,463,377 A | 10/1995 | Kronberg | |
| 5,486,166 A | 1/1996 | Bishop et al. | |
| 5,490,846 A | 2/1996 | Ellis et al. | |
| 5,760,694 A | 6/1998 | Nissim et al. | |
| 5,766,389 A | 6/1998 | Brandon et al. | |
| 5,820,973 A | 10/1998 | Dodge, II et al. | |
| 6,645,190 B1 | 11/2003 | Olson et al. | |
| 6,677,859 B1 | 1/2004 | Bensen | |
| 7,394,391 B2 | 7/2008 | Long | |
| 7,489,252 B2 | 2/2009 | Long et al. | |
| 7,595,734 B2 | 9/2009 | Long et al. | |
| 2002/0070868 A1 | 6/2002 | Jeutter et al. | |
| 2004/0064114 A1 | 4/2004 | David et al. | |
| 2004/0113801 A1 | 6/2004 | Gustafson et al. | |
| 2006/0058745 A1 | 3/2006 | Pires | |
| 2007/0024457 A1 | 2/2007 | Long et al. | |
| 2007/0083174 A1 | 4/2007 | Ales, III et al. | |
| 2007/0252710 A1 | 11/2007 | Long et al. | |
| 2007/0282286 A1 | 12/2007 | Collins et al. | |
| 2008/0243099 A1 | 10/2008 | Tippey et al. | |
| 2008/0269702 A1 | 10/2008 | Ales et al. | |
| 2008/0297325 A1 | 12/2008 | Torstensson et al. | |
| 2009/0124990 A1 | 5/2009 | Feldkamp et al. | |
| 2010/0164733 A1 | 7/2010 | Ales et al. | |
| 2010/0168694 A1 | 7/2010 | Gakhar et al. | |
| 2010/0168702 A1 | 7/2010 | Ales, III et al. | |
| 2010/0264369 A1 | 10/2010 | Zhang | |

FOREIGN PATENT DOCUMENTS

WO    00/37009    6/2000
WO    2009/063358    5/2009

OTHER PUBLICATIONS

Written Opinion and Search Report for PCT/IB2011/054337 dated May 21, 2012.

*Primary Examiner* — Jackie Ho
*Assistant Examiner* — Kathryn E Ditmer
(74) *Attorney, Agent, or Firm* — Dority & Manning, P.A.

(57) ABSTRACT

The present subject matter relates to absorbent articles and signaling devices for use therewith. The signaling device includes one or more non-invasive sensors configured to detect the presence of a substance, such as a body fluid, in the absorbent article. The signaling device can provide an audible and/or visible alert to the user of the absorbent article when it detects the presence of a substance. The absorbent article includes one or more identifiable characteristics the presence of which permits operation of the signaling device. In this manner, the present disclosure provides for product and signaling device matching for use.

4 Claims, 12 Drawing Sheets

APPARATUS AND METHOD FOR PRODUCT AND SIGNALING DEVICE MATCHING

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent articles, especially those sold under the tradename HUGGIES™ by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators, for example, may include alarm devices that are designed to assist parents or attendants identify a wet diaper condition quickly upon insult. The devices produce either a visual or an audible signal.

In some embodiments, for instance, inexpensive conductive threads, foils, or paper have been placed in the absorbent articles in the machine direction. The conductive materials serve as conductive leads for a signaling device and form an open circuit in the article that can be closed when a body fluid, such as urine, closes the circuit. In these embodiments, although the absorbent articles may be disposable, the signaling devices are not. Thus, the signaling devices are intended to be removed from the article and reattached to a subsequent article.

Incorporating conductive leads into absorbent articles, however, has caused various problems. For example, absorbent articles are typically mass produced on very fast moving machinery. Incorporating conductive leads into an absorbent article at conventional machine speeds has been problematic.

In addition, packaged absorbent articles are typically fed through a metal detector to ensure that there are no foreign objects contained in the package. If the conductive leads are made from or contain a metal, the metal detector can be activated registering a false positive. The incorporation of metallic materials into absorbent articles can also cause problems for those wearing the garments when attempting to pass through security gates that include metal detectors.

Several technologies have enabled wetness detection with little to no product alteration using non-invasive sensors that can be removably placed on the absorbent article. By way of example, U.S. Patent Application Publication No. 2010/0168694, which is incorporated herein by reference for all purposes, discloses an infrared wetness detection system for an absorbent article that includes a non-invasive sensor that measures infrared reflectance at some depth within an absorbent article, U.S. Patent Application Publication No. 2010/0164733, which is incorporated herein by references for all purposes, discloses the use of various sensors, such as a temperature sensor, a conductivity sensor, a humidity sensor, a chemical sensor, a vibration sensor, or a material expansion sensor placed on an outside cover of an absorbent article. U.S Patent Application Publication No. 2009/0124990, which is incorporated by reference herein for all purposes, discloses the use of an induction coil sensor for wetness detection in an absorbent article. Commonly owned U.S. patent application Ser. No. 12/648,645, which is incorporated herein by reference for all purposes, discloses a non-invasive capacitive sensor system and associated circuitry for wetness detection, In these embodiments, complexity falls to the signaling devices attached to the absorbent articles.

While a non-invasive signaling device provides many advantages, problems can be encountered in properly associating a particular signaling device with a proprietary product. In particular, due to the non-invasive nature of such signaling devices, a proprietary signaling device can be used with any absorbent article, regardless of the manufacturer or source of the absorbent article. Moreover, non-invasive signaling devices can be used on products that have not been safety cleared for use with a signaling device.

Thus, a need exists for an apparatus and method that enables product and signaling device matching for use.

SUMMARY

Aspects and advantages of the invention will be set forth in part in the following description, or may be obvious from the description, or may be learned through practice of the invention.

One exemplary embodiment of the present disclosure is directed to an absorbent article. The absorbent article includes a chassis having an outer cover with an interior surface and an exterior surface. The chasses further includes an absorbent structure positioned adjacent the interior surface of the outer cover. The absorbent article includes an attachment zone configured to receive a non-invasive signaling device configured to detect the presence of a substance. For instance, in a particular embodiment, the non-invasive signaling device detects the presence of a substance by monitoring changes in infrared light reflectance due to the presence of a substance, such as an insult, in the absorbent article. In another embodiment, the non-invasive signaling device can include a capacitive sensor adapted to sense a change in capacitance due to the presence of a substance, such as an insult, in the absorbent article. In yet another embodiment, the non-invasive signaling device can include an inductive sensor adapted to sense a change in inductance due to the presence of a substance, such as an insult, in the absorbent article. The attachment zone can include a design scheme to assist a user to properly align the non-invasive signaling device with the absorbent article.

In accordance with exemplary aspects of the present disclosure, the absorbent article includes at least one identifiable characteristic, the presence of which permits operation of the non-invasive signaling device. For instance, in one exemplary embodiment, the at least one identifiable characteristic includes at least one predefined color on the absorbent article. The signaling device can be permitted to operate when the signaling device detects the presence of the at least one predefined color on the absorbent article. The at least one color can be part of a design scheme configured to aid in alignment of the non-invasive signaling device with the absorbent article.

In another embodiment, the at least one identifiable characteristic includes the presence of one or more UV patterns, (e.g. UV inks or UV adhesives) arranged in an identifiable pattern on the absorbent article. The UV patterns can be configured to fluoresce when illuminated with electromagnetic energy at a particular frequency. The non-invasive signaling device can be configured to illuminate the UV patterns with electromagnetic energy sufficient to fluoresce the UV pattern. The non-invasive signaling device can further include an optical sensor configured to detect the presence of the fluoresced UV pattern.

In another embodiment, the at least one identifiable characteristic includes an infrared light reflectance of a material on the absorbent article. For instance, in a particular embodiment, the absorbent article can include a material having a particular infrared absorbance/reflectance. The non-invasive signaling device can include an infrared energy source configured to illuminate the material with infrared energy and detect the infrared light reflectance of material. If the infrared light reflectance falls within a predefined range, the non-invasive signaling device can be permitted to operate.

In still another embodiment, the at least one identifiable characteristic includes one or more electrical characteristics of a conductive pattern (e.g. conductive ink or conductive adhesive) on the absorbent article. The conductive pattern can be arranged to form a conductive pattern on the absorbent article. The non-invasive signaling device can include an electrical property sensor, such as a conductivity sensor, an inductive sensor or a capacitive sensor, configured to detect electrical characteristics of the conductive pattern. If the electrical characteristics fall within a predefined range of parameters, the non-invasive signaling device can be permitted to operate.

Another exemplary embodiment of the present disclosure is directed to a signaling device for sensing and indicating the presence of a substance in an absorbent article. The signaling device includes a housing and a first non-invasive sensor configured to detect the presence of a substance in the absorbent article. For instance, in a particular embodiment, the non-invasive signaling device detects the presence of a substance by monitoring changes in infrared light reflectance due to the presence of a substance, such as an insult, in the absorbent article. In another embodiment, the non-invasive signaling device can include a capacitive sensor adapted to sense a change in capacitance due to the presence of a substance, such as an insult, in the absorbent article. In another embodiment, the non-invasive signaling device can include an inductive sensor adapted to sense a change in inductance due to the presence of a substance, such as an insult, in the absorbent article.

In accordance with exemplary aspects of the present disclosure, the signaling device includes a second non-invasive sensor configured to detect the presence of at least one identifiable characteristic on the absorbent article. The presence of the at least one identifiable characteristic permits operation of the first non-invasive sensor.

For instance, in a particular embodiment, the second non-invasive sensor can include a colorimeter sensor configured to detect the presence of at least one predefined color on the absorbent article. The signaling device can be configured to active the first non-invasive sensor when the colorimeter detects the presence of the at least one predefined color on the absorbent article. The signaling device can further include a light source configured to illuminate the at least one predefined color on the absorbent article so that it can be detected by the colorimeter. The at least one predefined color can be part of a design scheme configured to aid in the alignment of the signaling device on the absorbent article.

In another embodiment, the signaling device includes a light source configured to illuminate a UV pattern (e.g. UV ink or UV adhesive) on the absorbent article with electromagnetic energy sufficient to fluoresce the UV pattern. The second non-invasive sensor can include an optical sensor configured to detect the presence of the pattern of UV pattern when the pattern of UV pattern is illuminated with the light source. The signaling device can be configured to activate the first non-invasive sensor when the optical sensor detects the presence of the fluoresced pattern of UV pattern.

In another embodiment, the signaling device can include an infrared source configured to illuminate a material on the absorbent article with infrared light. The signaling device can further include an infrared detector configured to detect the infrared light reflectance of the material. The signaling device can be configured to activate the first non-invasive sensor when the infrared reflectance of the material falls within a predefined range.

In still another embodiment, the second non-invasive sensor can include an electrical property sensor, such as a conductivity sensor, an inductive sensor or a capacitive sensor, configured to detect an electrical characteristic of one or more conductive patterns on the absorbent article. The signaling device can be configured to activate the first non-invasive sensor when the electrical property sensor detects a predefined electrical characteristic associated with the one or more conductive patterns.

A further exemplary embodiment of the present disclosure is directed to a method of matching a signaling device with an absorbent article. The method includes placing a signaling device on the absorbent article. The signaling device includes a first non-invasive sensor configured to detect the presence of a substance, such as an insult, in the absorbent article. For instance, in a particular embodiment, the non-invasive signaling device detects the presence of a substance by monitoring changes in infrared light reflectance due to the presence of a substance, such as an insult, in the absorbent article. In another embodiment, the non-invasive signaling device can include a capacitive sensor adapted to sense a change in capacitance due to the presence of a substance, such as an insult, in the absorbent article. In another embodiment, the non-invasive signaling device can include an inductive sensor adapted to sense a change in inductance due to the presence of a substance, such as an insult, in the absorbent article.

In accordance with an exemplary aspect of the present disclosure, the signaling device includes a second non-invasive sensor. The method includes detecting the presence of one or more identifiable characteristics on the absorbent article using the second non-invasive sensor and activating the first non-invasive sensor when the second non-invasive sensor detects the presence of one or more identifiable characteristics of the absorbent article.

In a particular embodiment, detecting the presence of one or more identifiable characteristics can include detecting the presence of one or more predefined colors on the absorbent article. For instance, the method can include illuminating the absorbent article with light energy from a light source and determining the presence of one or more predefined identifiable characteristics with a colorimeter.

In another embodiment, detecting the presence of one or more identifiable characteristics can include detecting the presence of one or more UV patterns on the absorbent article. For instance, the method can include illuminating the UV inks with light energy at a frequency sufficient to fluoresce the UV patterns and determining the presence of the fluoresced UV patterns using an optical sensor.

In another embodiment, detecting the presence of one or more identifiable characteristics can include detecting infrared light energy reflected from a material on the absorbent article. For instance, the method can include illuminating a material on an absorbent article with infrared energy and monitoring the infrared light reflectance of the material with an infrared sensor. The method can include activating the first non-invasive sensor of the signaling device when the detected infrared light energy falls within a predefined range.

In still another embodiment, detecting the presence of one or more identifiable characteristics can include detecting one or more electrical characteristics of a conductive ink on the absorbent article. The conductive ink can be arranged to form a conductive pattern. The method can include detecting electrical characteristics of the conductive pattern using an electrical property sensor and activating the first non-invasive sensor if the electrical property sensor detects a predefined electrical characteristic.

Variations and modifications can be made to these exemplary embodiments of the present disclosure.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
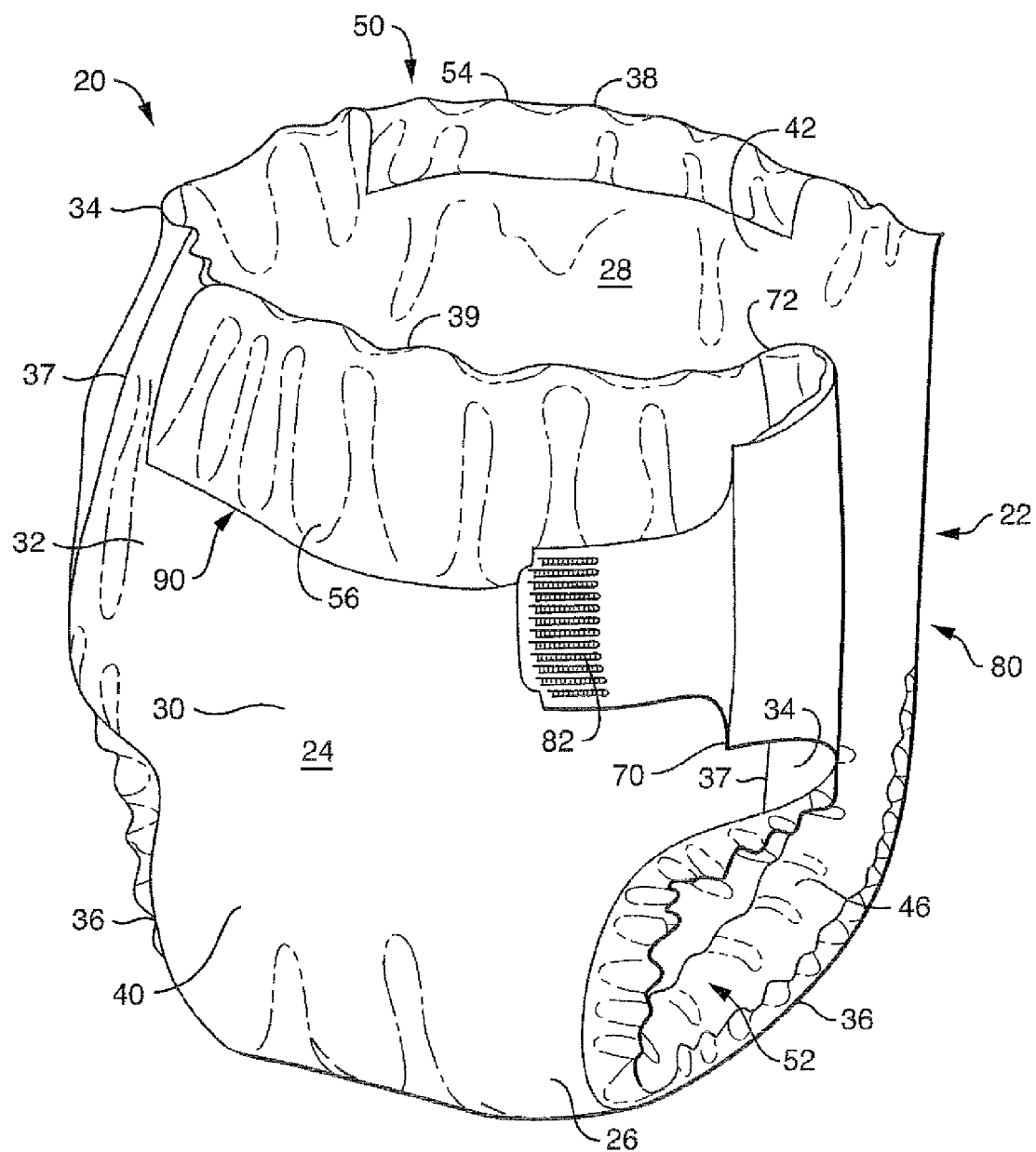
FIG. 1 is a rear perspective view of one embodiment of an absorbent article made in accordance with an exemplary embodiment of the present disclosure.

Repeat use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

The present disclosure is generally directed to matching a signaling device with an absorbent article. The absorbent article may be, for instance, a diaper, a training pant, an incontinence product, a feminine hygiene product, a medical garment, a bandage, and the like. A non-invasive signaling device can be placed on the absorbent article to determine the presence of a substance, such a body fluid, in the absorbent article. The signaling device can provide some type of audible and/or visible signal that indicates to the user the presence of a body fluid in the absorbent article.

The use of a non-invasive signaling device enables detection with little to no product alteration of the absorbent article. For instance, in a particular embodiment, the non-invasive signaling device detects the presence of a substance by monitoring changes in infrared light reflectance due to the presence of a substance in the absorbent article. In another embodiment, the signaling device can include a non-invasive sensor, such as a temperature sensor, a conductivity sensor, a humidity sensor, a chemical sensor, a vibration sensor, or a material expansion sensor, to detect the presence of a substance in the absorbent article. In another embodiment, the non-invasive signaling device can include a capacitive sensor adapted to sense a change in capacitance due to the presence of a substance in the absorbent article. In still another embodiment, the non-invasive signaling device can include a capacitive sensor adapted to sense a change in inductance due to the presence of a substance in the absorbent article.

Although non-invasive signaling devices provide many advantages, the non-invasive nature of the signaling devices allows the device to be used with any absorbent article, regardless of the manufacturer or source of the absorbent article. For instance, a proprietary signaling device could be used to detect the presence of a substance in an absorbent article manufactured by a competitor. This can lead to problems and safety concerns resulting from the use of a signaling device with unknown absorbent articles that are not specially designed to be used with the signaling device.

The subject matter of the present disclosure prevents the use of a signaling device on an unauthorized product by detecting the presence of one or more identifiable characteristics on the absorbent article. The presence of one or more identifiable characteristics on the absorbent article, in essence, serves as a key that unlocks the primary functionality of the signaling device. In particular, an absorbent article can be manufactured with a particular identifiable characteristic that can be sensed or detected by the non-invasive signaling device. When the non-invasive signaling device detects the presence of the identifiable characteristic on the absorbent article, the non-invasive signaling device is permitted to operate to detect the presence of a substance in the absorbent article. If the signaling device is used on an absorbent article that does not include the identifiable characteristic, the non-invasive signal will not operate, preventing the use of a proprietary signaling device on an unauthorized product.

Figure 2:
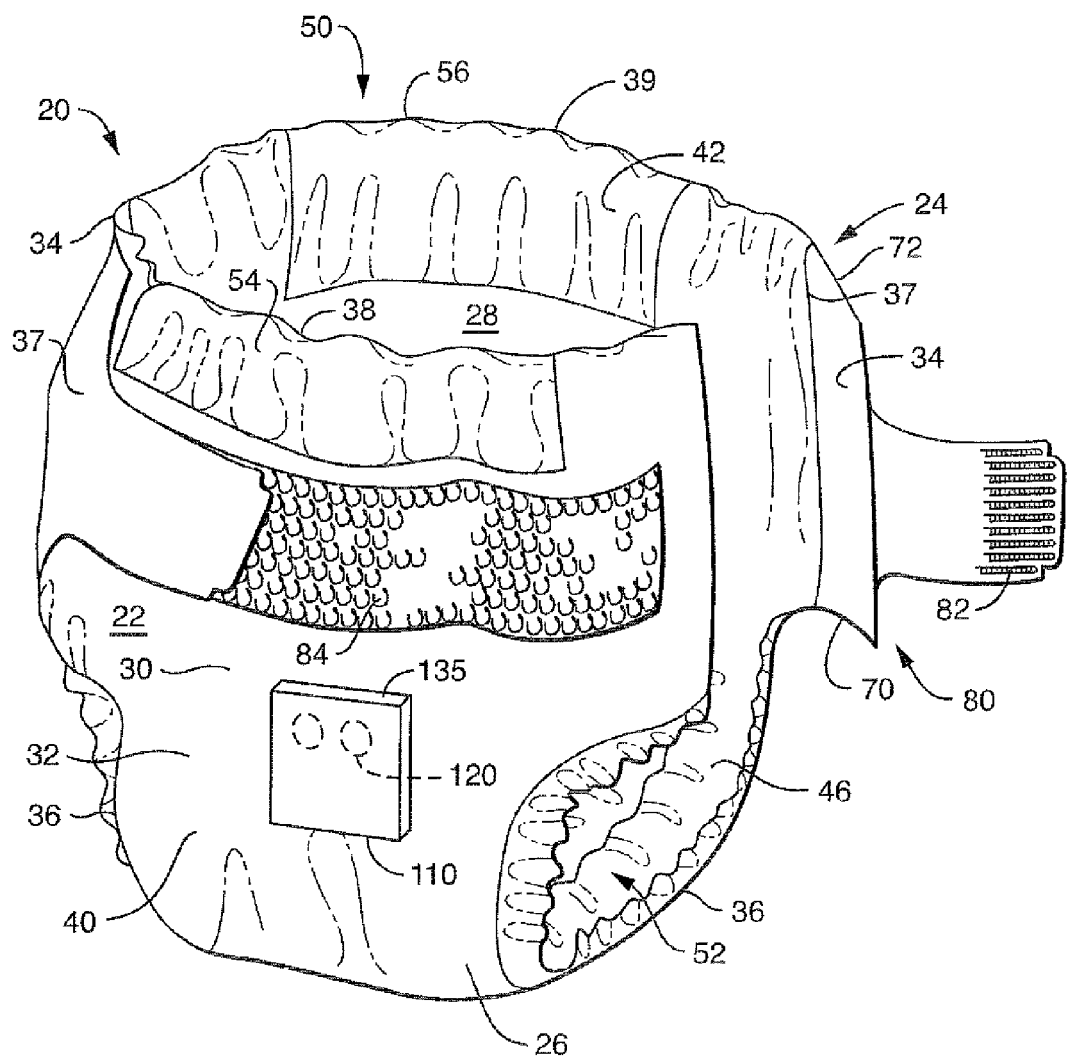
FIG. 2 is a front perspective view of the absorbent article illustrated in FIG. 1 including one aspect of a wetness indicator of the present disclosure.

Referring to FIGS. 1 and 2, for exemplary purposes, an absorbent article 20 that can be used in conjunction with signaling systems of the present disclosure is shown. The absorbent article 20 can be disposable or not. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present disclosure.

By way of illustration only, various materials and methods for constructing absorbent articles such as the absorbent article 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson at al. which are incorporated herein by reference to the extent they are consistent (i.e., not in conflict) herewith.

Figure 3:
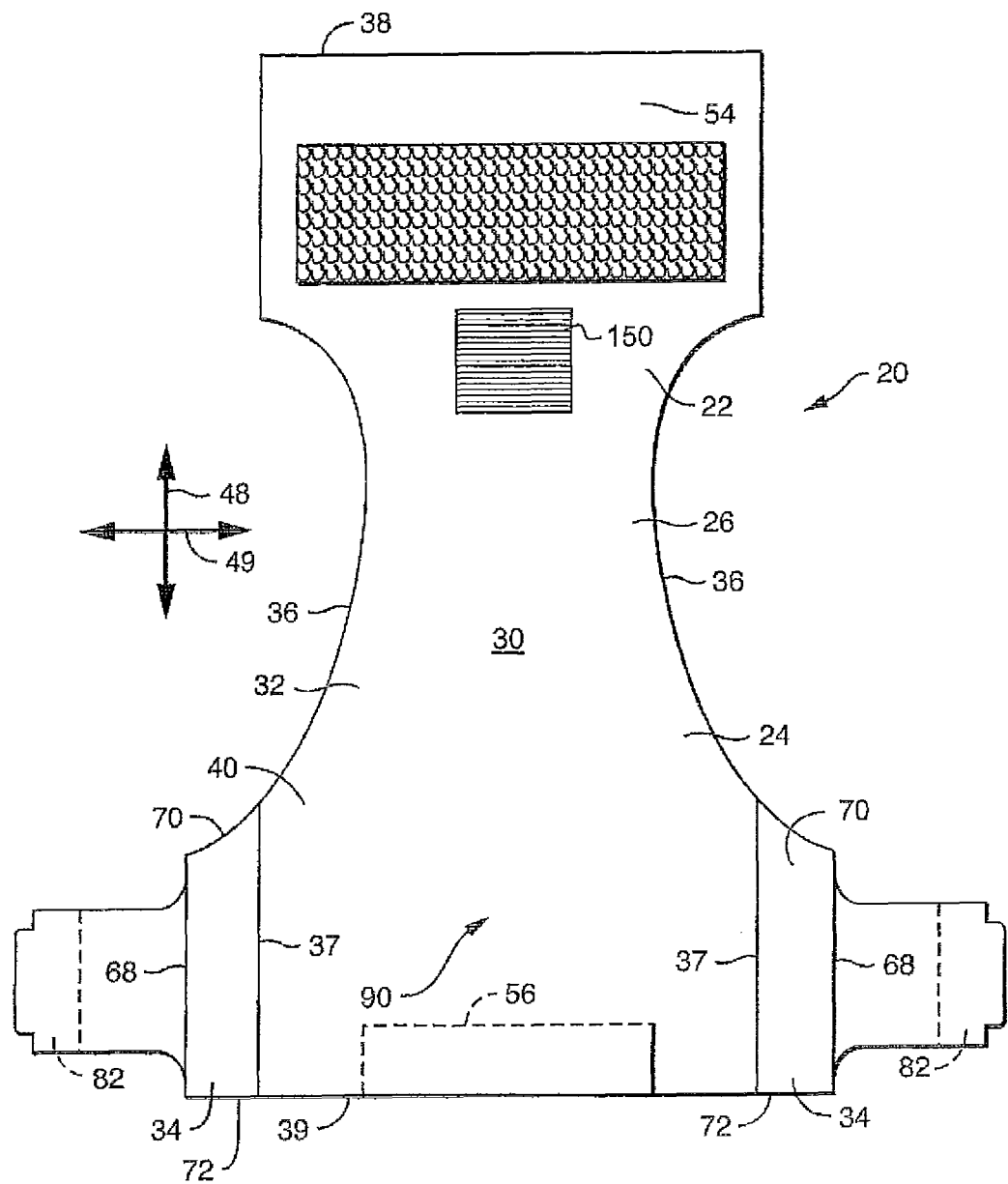
FIG. 3 is a plan view of the absorbent article shown in FIG. 1 with the article in an unfastened, unfolded and laid flat condition showing the surface of the article that faces away from the wearer.
Figure 4:
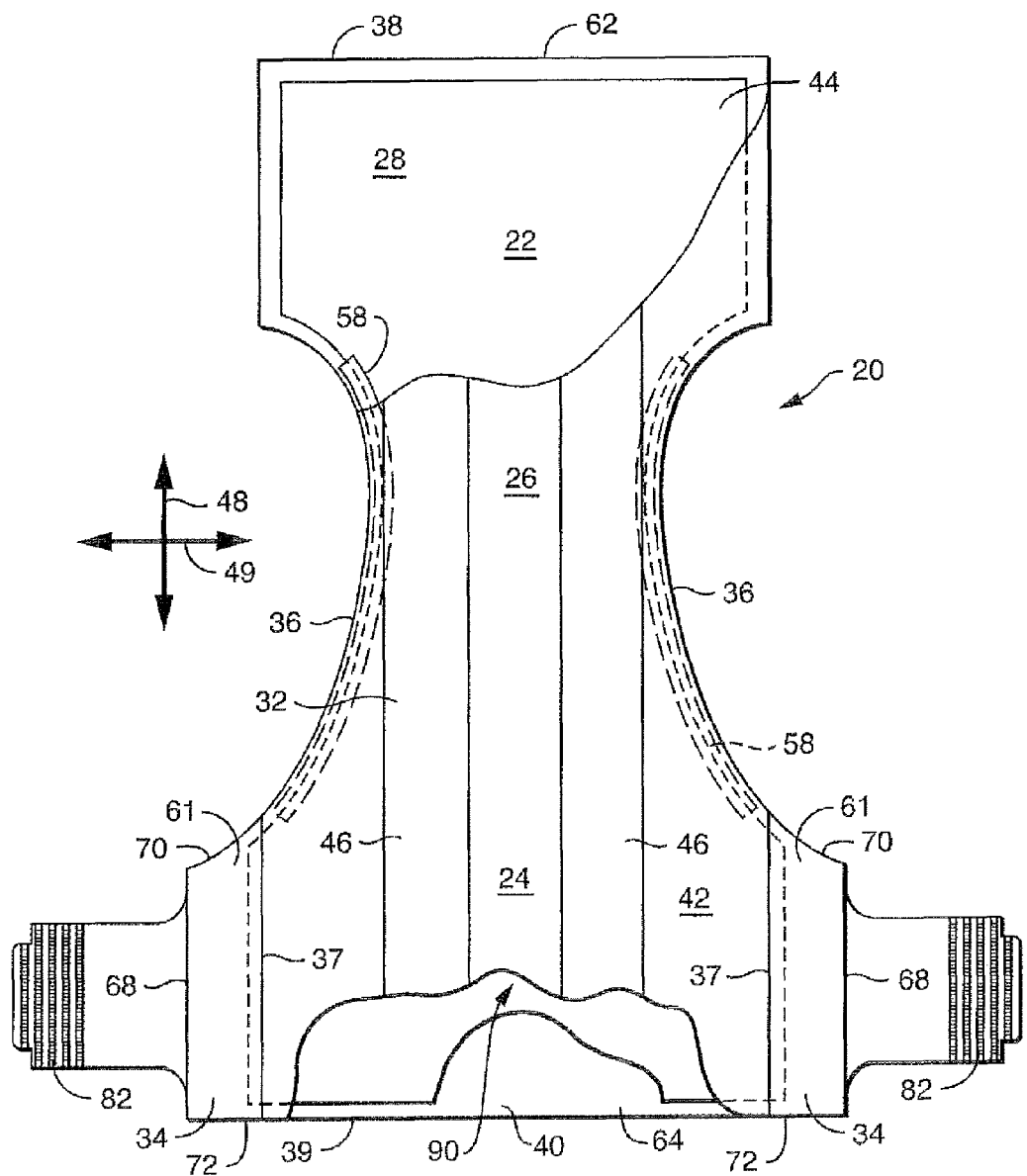
FIG. 4 is a plan view similar to FIG. 3 showing the surface of the absorbent article that faces the wearer when worn and with portions cut away to show underlying features.

An absorbent article 20 is representatively illustrated in FIG. 1 in a partially fastened condition. The absorbent article 20 shown in FIGS. 1 and 2 is also represented in FIGS. 3 and 4 in an opened and unfolded state. Specifically, FIG. 3 is a plan view illustrating the exterior side of the absorbent article 20, while FIG. 4 illustrates the interior side of the absorbent article 20. As shown in FIGS. 3 and 4, the absorbent article 20 defines a longitudinal direction 48 that extends from the front of the article when worn to the back of the article. Orthogonal to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, that, when worn, wholly or partially cover or encircle the waist or mid-lower torso of the wearer. The crotch region 26 generally is that portion of the absorbent article 20 that, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that can be joined to the outer cover 40 in a superimposed relation therewith by adhesives, ultrasonic bonds, thermal bonds or other conventional techniques. Referring to FIG. 4, the liner 42 can suitably be joined to the outer cover 40 along the perimeter of the chassis 32 to form a front waist seam 62 and a back waist seam 64. As shown in FIG. 4, the liner 42 can suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article 20. The chassis 32 can further include an absorbent structure 44 particularly shown in FIG. 4 disposed between the outer cover 40 and the bodyside liner 42 for absorbing liquid body exudates exuded by the wearer, and can further include a pair of containment flaps 46 secured to the bodyside liner 42 for inhibiting the lateral flow of body exudates.

The elasticized containment flaps 46 as shown in FIG. 4 define a partially unattached edge that assumes an upright configuration in at least the crotch region 26 of the absorbent article 20 to form a seal against the wearer's body. The containment flaps 46 can extend longitudinally along the entire length of the chassis 32 or can extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 can also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 can include a plurality of dry-spun coalesced multifilament spandex elastomeric threads sold under the trade name LYCRA and available from Invista, Wilmington, Del., U.S.A.

In some aspects, the absorbent article 20 can further include a surge management layer (not shown) that can be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that can be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 can be stretched around the waist and/or hips of a wearer to secure the garment in place. As shown in FIGS. 3 and 4, the elastic side panels are attached to the chassis along a pair of opposing longitudinal edges 37. The side panels 34 can be attached or bonded to the chassis 32 using any suitable bonding technique. For instance, the side panels 34 can be joined to the chassis by adhesives, ultrasonic bonds, thermal bonds, or other conventional techniques.

In an alternative aspect, the elastic side panels can also be integrally formed with the chassis 32. For instance, the side panels 34 can include an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 can alternatively be connected to the front region of the article 20 and extend over the back region when the article is donned.

With the absorbent article 20 in the fastened position as partially illustrated in FIGS. 1 and 2, the elastic side panels 34 can be connected by a fastening system 80 to define a 3-dimensional absorbent article configuration having a waist opening 50 and a pair of leg openings 52. The waist opening 50 of the article 20 is defined by the waist edges 38 and 39 that encircle the waist of the wearer.

In the aspects shown in the figures, the side panels are releasably attachable to the front region 22 of the article 20 by the fastening system. It should be understood, however, that in other aspects the side panels can be permanently joined to the chassis 32 at each end. The side panels can be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 can be suitably curved and/or angled relative to the lateral direction 49 to provide a better fit around the wearer's legs. However, it is understood that only one of the leg end edges 70 can be curved or angled, such as the leg end edge of the back region 24, or alternatively, neither of the leg end edges can be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 can be slanted or curved as desired. Ultimately, the side panels 34 are generally aligned with a waist region 90 of the chassis.

The fastening system 80 can include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 can be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 can include loop fasteners and the second fastening components 84 can be complementary hook fasteners. In another aspect, the fastening components 82, 84 can be interlocking similar surface fasteners, or adhesive and cohesive fastening elements such as an adhesive fastener and an adhesive-receptive landing zone or material; or the like.

In addition to possibly having elastic side panels, the absorbent article 20 can include various waist elastic members for providing elasticity around the waist opening. For example, as shown in the figures, the absorbent article 20 can include a front waist elastic member 54 and/or a back waist elastic member 56.

Referring to FIG. 2, a signaling device 110 has been located on the absorbent article 20. Signaling device 110 is configured to detect the presence of a substance in absorbent article 20 and to provide an audible and/or visible signal to the user of absorbent article 20 indicative of the presence of the substance. Signaling device 110 includes a housing 135 and one or more non-invasive sensors 120. Housing 135 can be used to house the various electronic and other components of signaling device 110.

Non-invasive sensors 120 are adapted to detect the presence of a substance, such as a body fluid, in the absorbent article 20. The non-invasive sensors 120 can be any non-invasive sensors 120 adapted to detect the presence of a substance in the absorbent article 20. For instance, in a particular embodiment, the non-invasive sensors 120 can be one or more of a temperature sensor, a conductivity sensor, a humidity sensor, a chemical sensor, a vibration sensor, or a material expansion sensor as disclosed in U.S. Patent Application Publication No. 2010/0164733, which is incorporated by reference for all purposes. In another embodiment, the non-invasive sensors 120 can include an infrared detector configured to monitor the infrared light reflectance of the absorbent article as disclosed in U.S. Patent Application Publication No. 2010/0168694, which is incorporated herein by reference for all purposes. In still another embodiment, the non-invasive sensors 120 can include a capacitive sensor configured to monitor electrical capacitance at some depth within an absorbent article which is disclosed in commonly assigned U.S. patent application Ser. No. 12/648,645 and is incorporated by reference herein for all purposes. In still another embodiment, the non-invasive sensors 120 can include an inductive sensor as disclosed in U.S. Patent Publication No. 2009/0124990, which is incorporated by reference herein for all purposes.

The non-invasive sensor 120 can be configured to be located at an attachment zone on the absorbent article, such as attachment zone 150 of FIG. 3. Attachment zone 150 can include a design scheme configured to assist the user in properly aligning the signaling device with the absorbent article 120 as disclosed in U.S. Patent Application Publication No. 2007/0282286, which is incorporated herein by reference for all purposes. The design scheme of attachment zone 150 can include any size, shape, coloring, graphics, and the like. For instance, in a particular, embodiment, design scheme can include a circular pattern printed with the color Orange Pantone #165U. The attachment zone 150 can include one or more identifiable characteristics, the presence of which permit operation of the signaling device.

The signaling device 110 may include one or more sensors that are configured to detect the presence of the one or more identifiable characteristics on the absorbent article 20. If the one or more identifiable characteristics are detected, the signaling device 110 can be activated such that the primary non-invasive sensors 120 of the signaling device 110 can detect the presence of a substance in the absorbent article 20 and can provide alerts to the user of the absorbent article.

Figure 5:
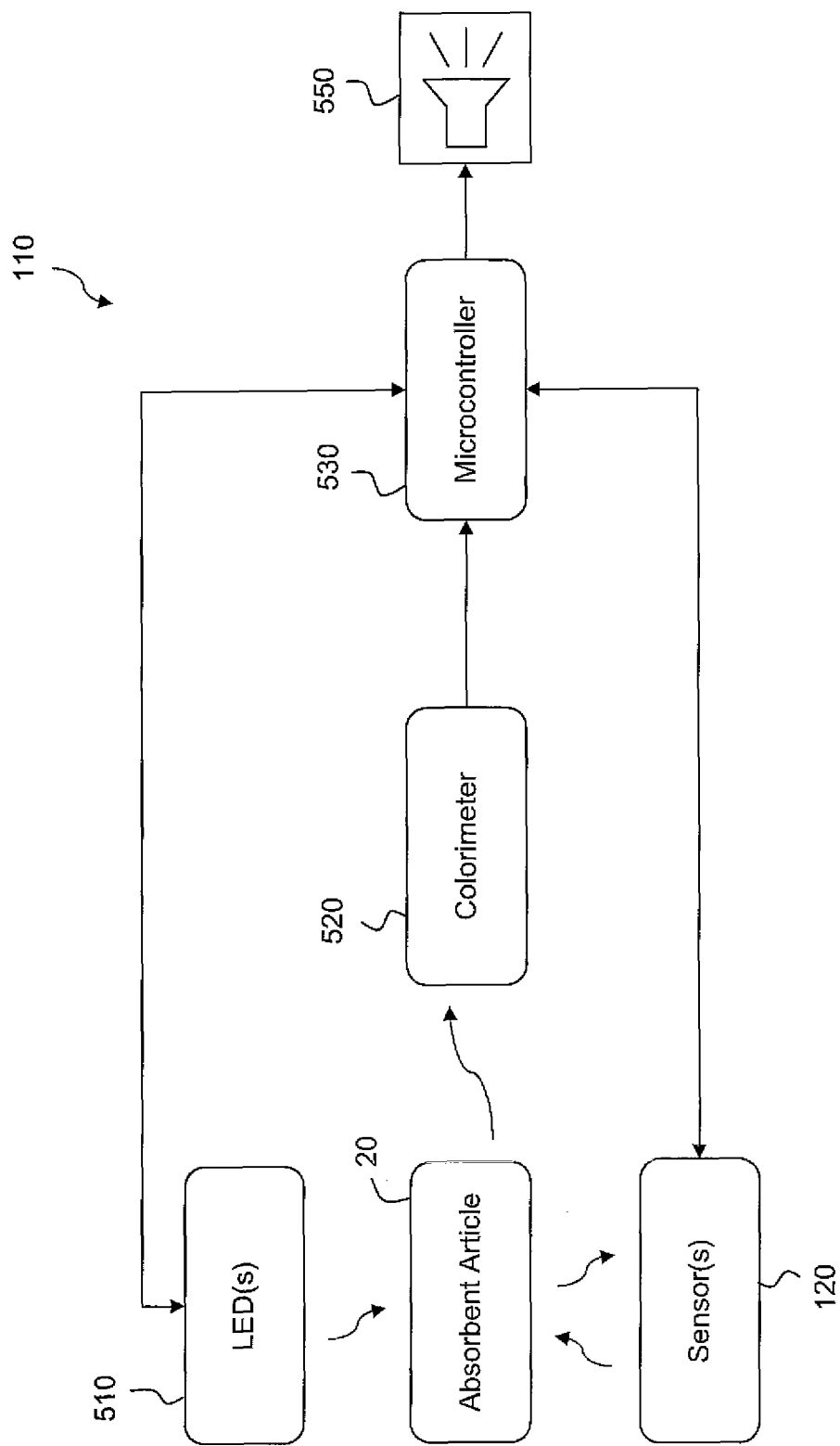
FIG. 5 is a block diagram of an exemplary signaling device according to an exemplary embodiment of the present disclosure.

In accordance with the present disclosure, the signaling system can have various configurations and designs. FIG. 5 depicts a block diagram of a first exemplary embodiment of a signaling device 110 that can detect the presence of one or more identifiable characteristics on an absorbent article. In particular, the signaling device 110 of FIG. 5 is configured to detect the presence of one or more predefined colors on the absorbent articles. For instance, the signaling device 110 can be configured to detect the presence of a circular pattern printed with the color Orange Pantone #165U. The predefined color can be located throughout on the absorbent article, allowing activation of the signaling device 110 anywhere on the product. Preferably, however, a graphic having a predefined color is printed on the absorbent article as part of the design scheme of attachment zone 150 of FIG. 3 for assisting the alignment of signaling device 110. A more secure method of matching can make use of a plurality of different predefined colors for detection by signaling device 110. The signaling device 110 of FIG. 5 is configured to detect the presence of the predefined color on the absorbent article. If the predefined color is present, the signaling device 110 is permitted to operate.

As illustrated in FIG. 5, the signaling device 110 of this exemplary embodiment includes an LED(s) 510 configured to illuminate the absorbent article with light. The reflected color of the absorbent article can be received by a colorimeter sensor 520. The colorimeter sensor 520 can include a photodiode, a phototransistor, a photodiode array, a phototransistor array or other suitable device for detecting the color of the reflected light. For instance, in a particular embodiment, the colorimeter sensor 520 can include a photodiode array with a color to frequency converter, such as a TCS 3210 manufactured by Texas Advanced Optoelectronics. In another embodiment, a single silicon photodiode such as OP980 made by Optek Inc. can be used to measure the intensity of light reflected from the absorbent article by an array of red, green, and blue LEDs.

The reflected signals received by the photodiode are amplified through various signal conditioning devices like transimpedance amplifier TI-OPA4348 made by Texas Instruments or MC6004 made by Microchip, Inc. The signals are provided to a microcontroller 530, such as PIC 16f876 or PIC24F16KA102 made by Microchip, Inc. The microcontroller 530 is coupled to the non-invasive sensors 120 of signaling device 110 and can control the sending of an alert through alert system 550 if the presence of a substance is detected in the absorbent article.

Figure 6:
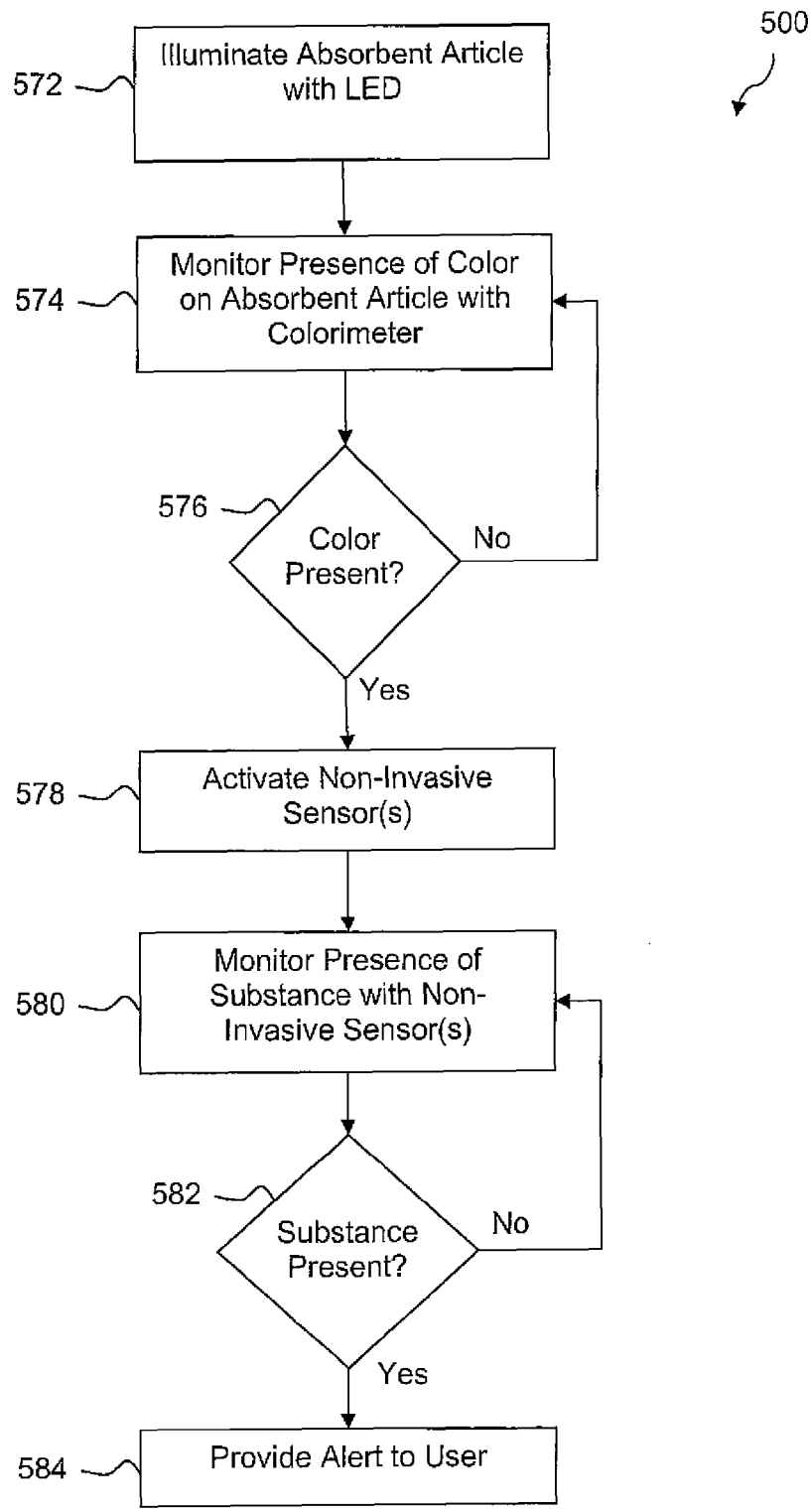
FIG. 6 is a flow diagram of exemplary method steps according to an exemplary embodiment of the present disclosure.

Microcontroller 530 is configured to control signaling device 110 to operate if the predefined color is detected on the absorbent article. FIG. 6 illustrates a flow diagram of an exemplary method 500 performed by microcontroller 530 in activating the signaling device 110. At 572, the microcontroller 530 can be configured to control the LED(s) 510 to illuminate the absorbent article. At 574, the microcontroller 530 monitors the presence of a predefined color on the absorbent article by analyzing signals received from colorimeter 520. At 576, the microcontroller 530 determines if the predefined color is present. If the predefined color is not detected, the microcontroller never activates the non-invasive sensors 120 of signaling device 110, preventing signaling device 110 from being used on an unauthorized product.

At 578, if the microcontroller 530 determines that the predefined color is present on the absorbent article, the microcontroller 530 activates the non-invasive sensors 120. At 580, the microcontroller 530 will monitor the presence of a substance in the absorbent article by analyzing signals received from the non-invasive sensors 120. As indicated at 582, the microcontroller 530 will determine whether a substance is present in the absorbent article based on the signals received from the non-invasive sensors 120. At 584, if a substance is detected, the microcontroller 530 will control alert system 550 to provide a visible and/or audible alert to the user of the absorbent article.

Figure 7:
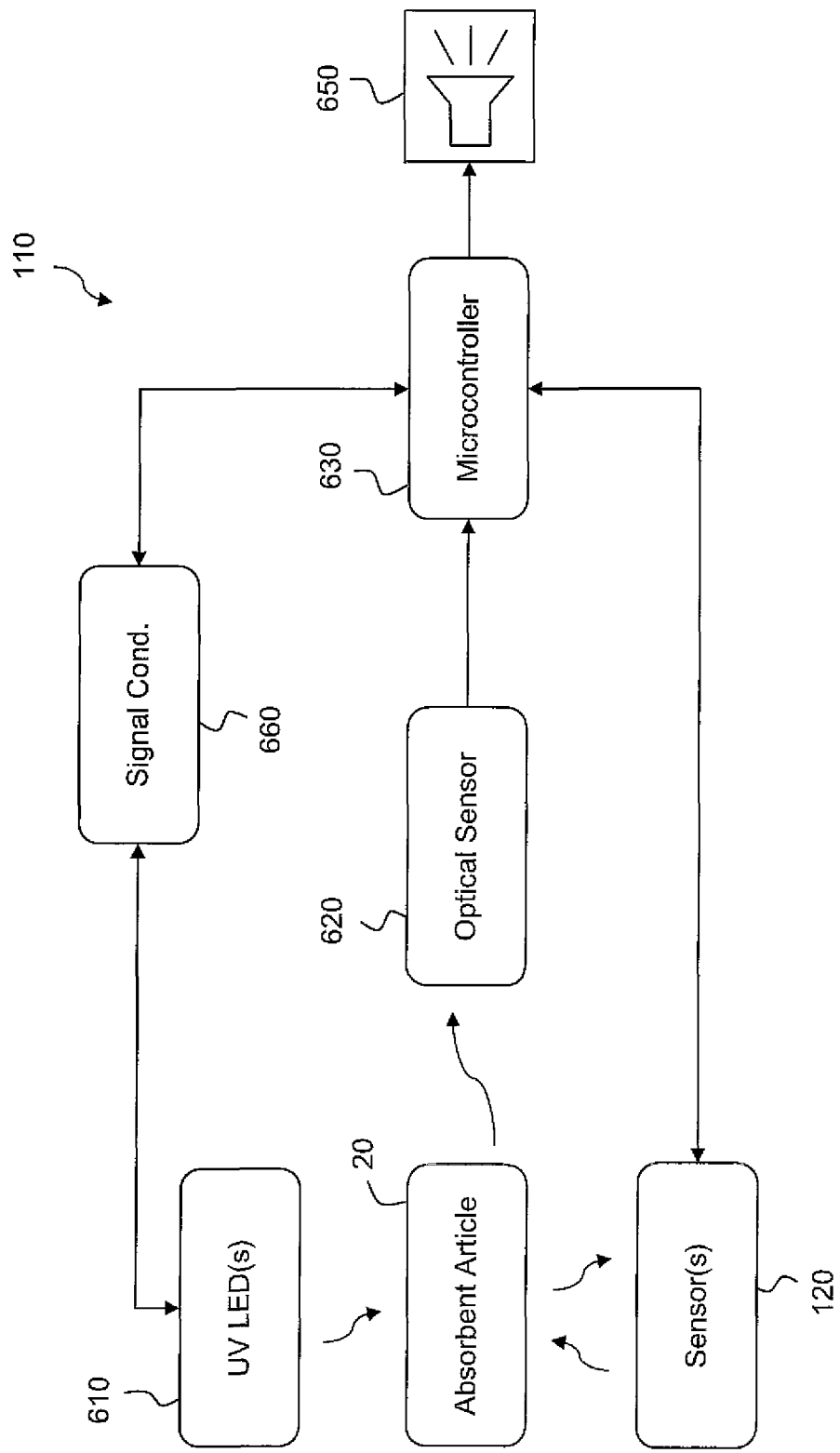
FIG. 7 is a block diagram of another exemplary signaling device according to an exemplary embodiment of the present disclosure.

FIG. 7 depicts a block diagram of another exemplary embodiment of a signaling device 110 that can detect the presence of one or more identifiable characteristics on an absorbent article. In particular, the signaling device 110 of FIG. 7 is configured to detect the presence of one or more UV patterns on the absorbent articles. The UV pattern can be formed from a UV ink or UV adhesive. For instance, UV pattern can be the UV adhesive disclosed in U.S. Patent Application Publication No. 2010/0264369, which is incorporated herein by reference. The UV pattern can be printed on the absorbent article at any location, such as at the attachment zone 150 of FIG. 3. The presence of a particular pattern of UV pattern on the absorbent article can be determined to activate the signaling device 110.

As illustrated in FIG. 7, the signaling device 110 of this exemplary embodiment includes UV LED(s) 610 configured to illuminate the absorbent article with light energy at a particular frequency. The frequency of the light energy should be tailored to fluoresce the UV pattern on the absorbent article. In particular, microcontroller 630 can control signal conditioning device 660 to modulate the LED(s) 610 at a particular frequency that is sufficient to flouresce the UV patterns on the absorbent article. The visible light produced from the fluorescence effect of the UV pattern can be detected by an optical sensor 620. Optical sensor 620 can include a photodiode array or other suitable device for detecting the presence of visible light from the fluoresced UV pattern. The optical sensor 620 can provide signals indicative of the detected light, through various signal conditioning devices, to microcontroller 630, such as a PIC 16F876A microcontroller. The microcontroller 630 is coupled to non-invasive sensors 120 of signaling device 110 and can control the sending of an alert through alert system 650 if the presence of a substance is detected in the absorbent article.

Figure 8:
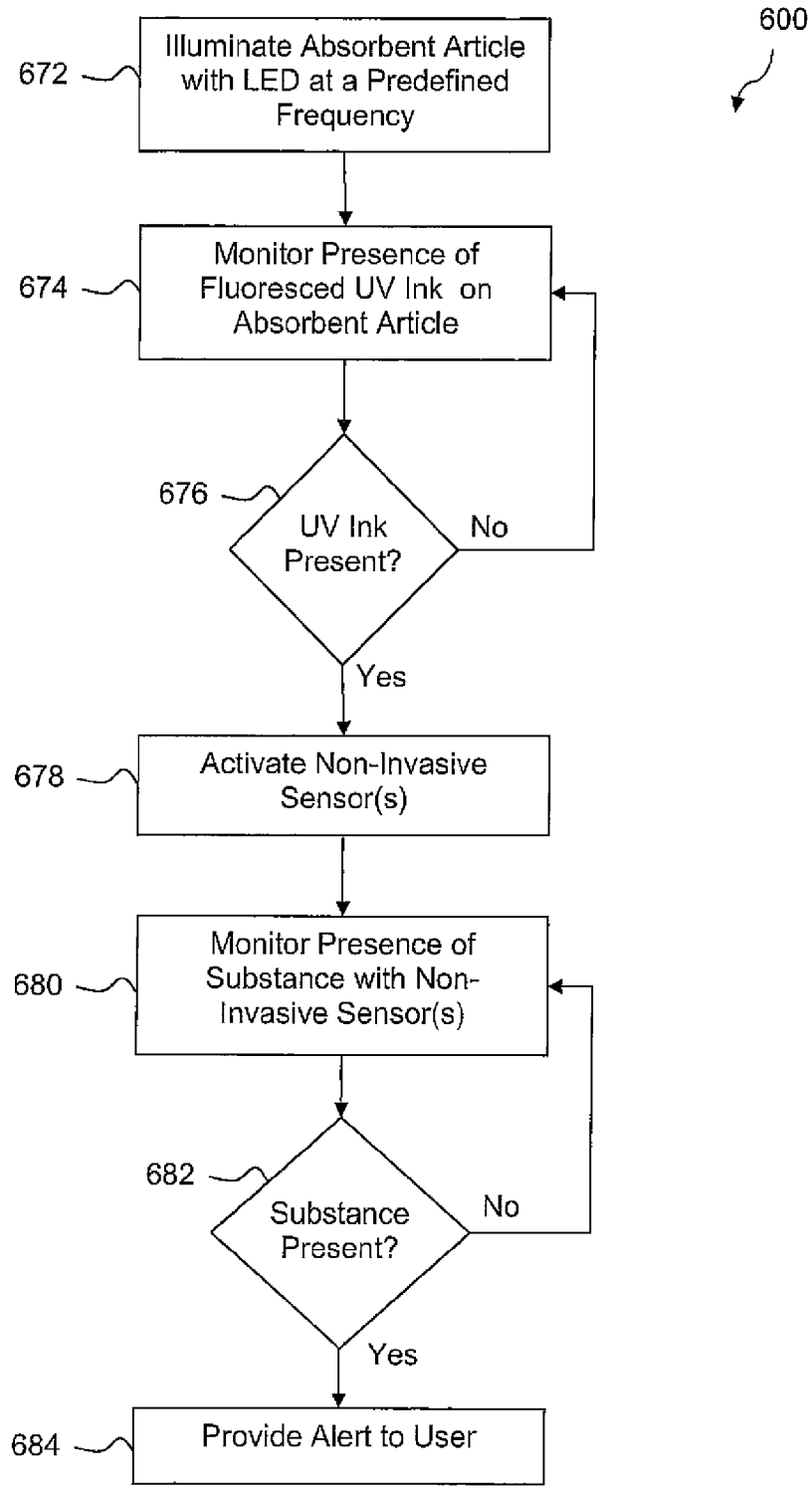
FIG. 8 is a flow diagram of exemplary method steps according to an exemplary embodiment of the present disclosure.

Microcontroller 630 is configured to activate the non-invasive sensors 120 of signaling device 120 if one or more fluoresced UV patterns are detected on the absorbent article. FIG. 8 illustrates a flow diagram of an exemplary method 600 performed by microcontroller 630 in activating the signaling device 110. At 672, the microcontroller 630 controls the UV LED(s) 610 to illuminate the absorbent article with light energy at a particular frequency. The frequency can be predefined such that it will illuminate the UV patterns printed on an authorized absorbent article. The frequency adds another layer of security to the signaling device 110 as UV patterns that are not configured to flouresce at the particular frequency emitted by the UV LED(s) 610 will not be detected, preventing operation of signaling device 110.

At 674, the microcontroller 630 monitors the presence of fluoresced UV patterns on the absorbent article by analyzing signals received from optical sensor 620. At 676 the microcontroller 630 determines if fluoresced UV patterns are present. If the fluoresced UV patterns are not detected, the microcontroller 630 never activates the non-invasive sensors 120 of signaling device 110, preventing signaling device 110 from being used on an unauthorized product.

At 678, if the microcontroller 630 determines that one or more fluoresced UV patterns are present on the absorbent article, the microcontroller 630 activates the non-invasive sensors 120. At 680, the microcontroller 630 will monitor the presence of a substance in the absorbent article by analyzing signals received from the non-invasive sensor 120. As indicated at 682, the microcontroller 630 will determine whether a substance is present in the absorbent article based on the signals received from the non-invasive sensors 120. At 684, if a substance is detected, the microcontroller 630 will control alert system 650 to provide a visible and/or audible alert to the user of the absorbent article.

Figure 9:
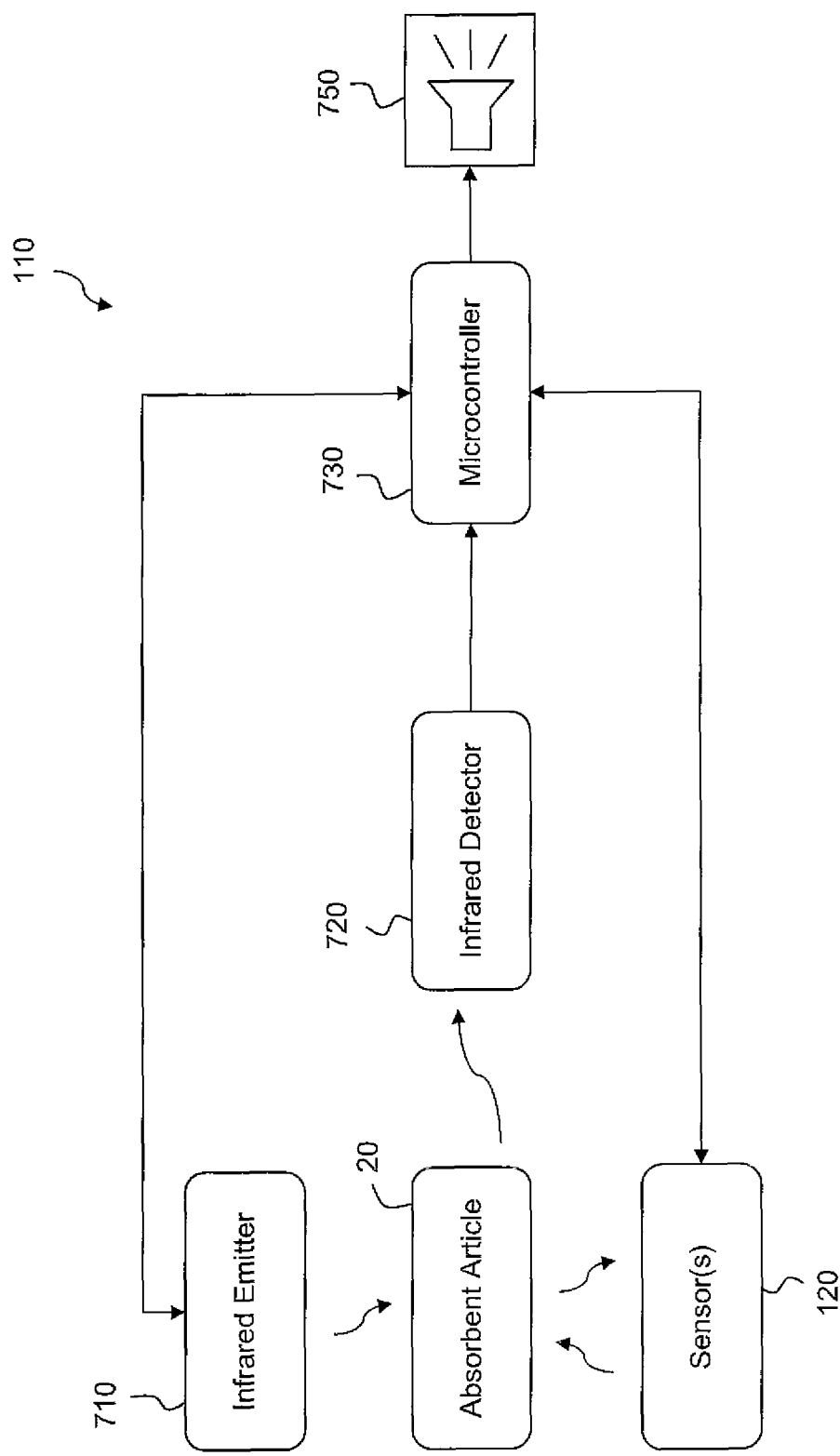
FIG. 9 is a block diagram of another exemplary signaling device according to an exemplary embodiment of the present disclosure.

FIG. 9 depicts a block diagram of another exemplary embodiment of a signaling device 110 that can detect the presence of one or more identifiable characteristics on an absorbent article. The signaling device 110 of FIG. 9 is configured to monitor the infrared light reflectance of a material on the absorbent article. If the infrared light reflectance falls within a predefined range, the signaling device 110 will be permitted to operate. For instance, a material having a specific range of infrared light reflectance can be included as part of the absorbent article, for instance at the attachment zone 150 of FIG. 3. The signaling device 110 can determine if this material is present by monitoring the infrared light reflectance characteristics of the absorbent article. The presence of the material with particular infrared light characteristics can permit operation of the signaling device 110.

As illustrated in FIG. 9, the signaling device 110 of this exemplary embodiment includes an infrared emitter 710 configured to illuminate the absorbent article with infrared light energy. The infrared emitter 710 can include an infrared generating light emitting diode (LED). At least a portion of the infrared energy emitted onto the material of the absorbent article is reflected and collected by an infrared detector 720, such as an infrared-detecting photo-transistor. Exemplary infrared detectors include the QRD114 made by Fairchild Semiconductors or the APDS-9120 made by Avago Technologies. The infrared detector 720 can provide signals indicative of the detected infrared light reflectance, through various signal conditioning devices, to microcontroller 730, such as a PIC 16F876A microcontroller. The microcontroller 730 is coupled to non-invasive sensors 120 of signaling device 110 and can control the sending of an alert through an alert system 750 if the presence of a substance is detected in the absorbent article.

Figure 10:
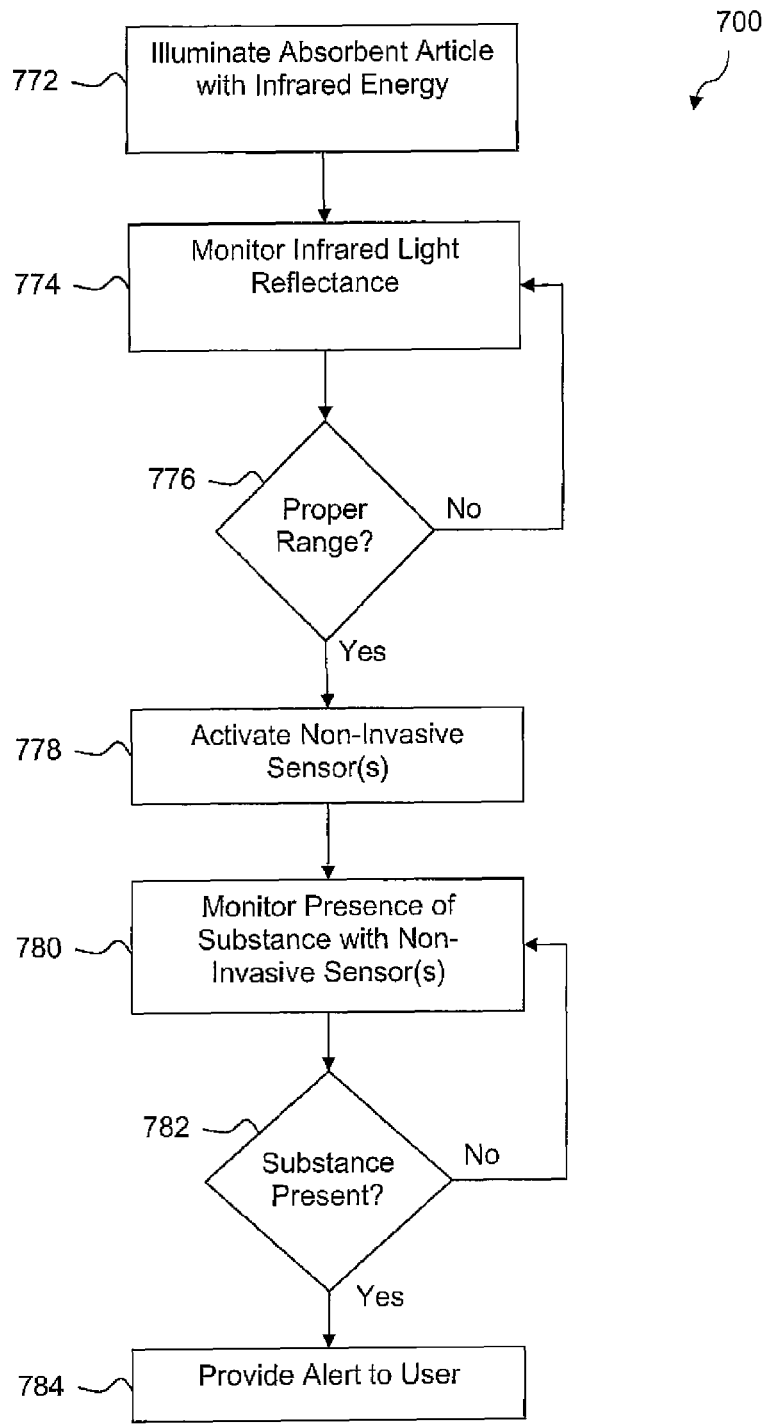
FIG. 10 is a flow diagram of exemplary method steps according to an exemplary embodiment of the present disclosure.

Microcontroller 730 is configured to activate the non-invasive sensors 120 of signaling device 110 if the infrared light reflectance detected from the absorbent article falls within a predefined range. FIG. 10 illustrates a flow diagram of an exemplary method 700 performed by microcontroller 730 in activating the signaling device 110. At 772, the microcontroller 730 controls infrared emitter 710 to illuminate the absorbent article with infrared energy. At 774, the microcontroller 730 monitors the infrared light reflectance from the absorbent article by analyzing signals received from infrared detector 720. At 776 the microcontroller 730 determines if the infrared light reflectance from the absorbent article falls within a predefined range. If the infrared light reflectance does not fall within the predefined range, the microcontroller 730 never activates the non-invasive sensors 120 of signaling device 110, preventing signaling device 110 from being used on an unauthorized product.

At 778, if the microcontroller 730 determines that the infrared light reflectance falls within the predefined range, the microcontroller 730 activates the non-invasive sensors 120. At 780, the microcontroller 730 will monitor the presence of a substance in the absorbent article by analyzing signals received from the non-invasive sensor 120. As indicated at 782, the microcontroller 730 will determine whether a substance is present in the absorbent article based on the signals received from the non-invasive sensors 120. At 784, if a substance is detected, the microcontroller 730 will control alert system 750 to provide a visible and/or audible alert to the user of the absorbent article.

Figure 11:
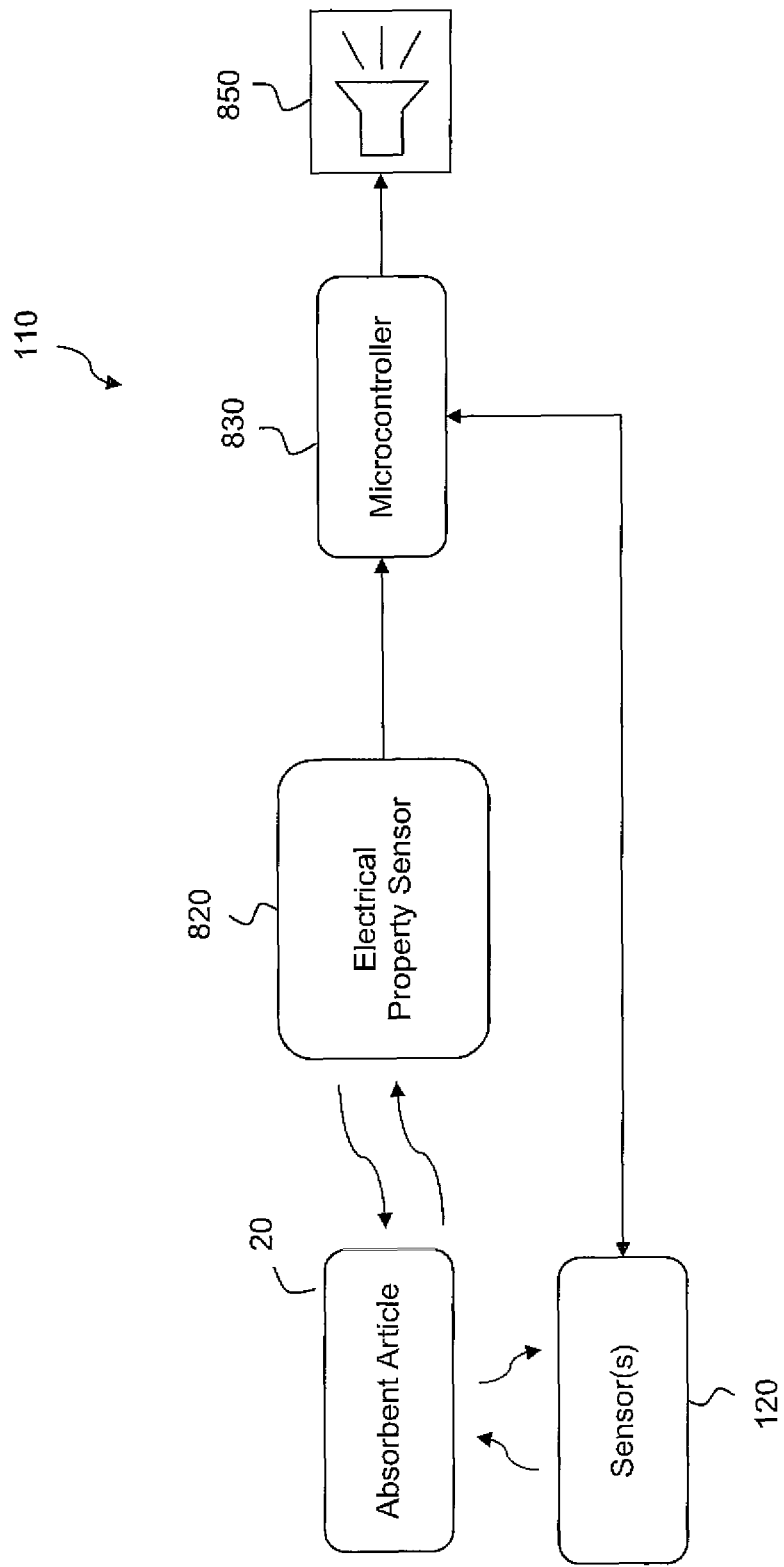
FIG. 11 is a block diagram of another exemplary signaling device according to an exemplary embodiment of the present disclosure.

FIG. 11 depicts a block diagram of another exemplary embodiment of a signaling device 110 that can detect the presence of one or more identifiable characteristics on an absorbent article. The signaling device 110 of FIG. 9 is configured to monitor electrical characteristics, such as capacitance, inductance, and/or conductivity, of conductive patterns printed on the absorbent article. If the electrical characteristics of the conductive patterns fall within a predefined range, the signaling device 110 will be permitted to operate.

For instance, in a particular embodiment, the absorbent article can include one or more conductive patterns arranged in a conductive pattern on the absorbent article, such as at attachment zone 150 of FIG. 3. The conductive pattern will have a particular "electrical fingerprint" based on the conductivity, capacitance, and/or inductance of the conductive pattern. The signaling device 110 can use one or more sensors to determine if the particular "electrical fingerprint" is present on the absorbent article. The presence of the "electrical fingerprint" can permit operation of the signaling device 110.

As illustrated in FIG. 11, the signaling device 110 of this exemplary embodiment includes an electrical property sensor 920, such as a conductivity sensor, capacitive sensor, and/or other sensor or combination of sensors, to detect electrical characteristics of conductive patterns on an absorbent article. The electrical property sensor 920 can be a part of other non-invasive sensors on the signaling device or can be stand alone. For instance, in a particular embodiment, the non-invasive sensors 120 of signaling device 110 include a plurality of capacitive sensors designed to detect a substance in the absorbent article. The electrical property sensor 920 can be one of the non-invasive capacitive sensors 120 configured to detect electrical properties of one or more conductive patterns on the absorbent article.

The electrical property sensor 820 can provide signals indicative of the electrical characteristics of the conductive pattern, through various signal conditioning devices, to microcontroller 830, such as a PIC 16F876A microcontroller. The microcontroller 830 is coupled to non-invasive sensors 120 of signaling device 110 and can control the sending of an alert through alert system 850 if the presence of a substance is detected in the absorbent article.

Figure 12:
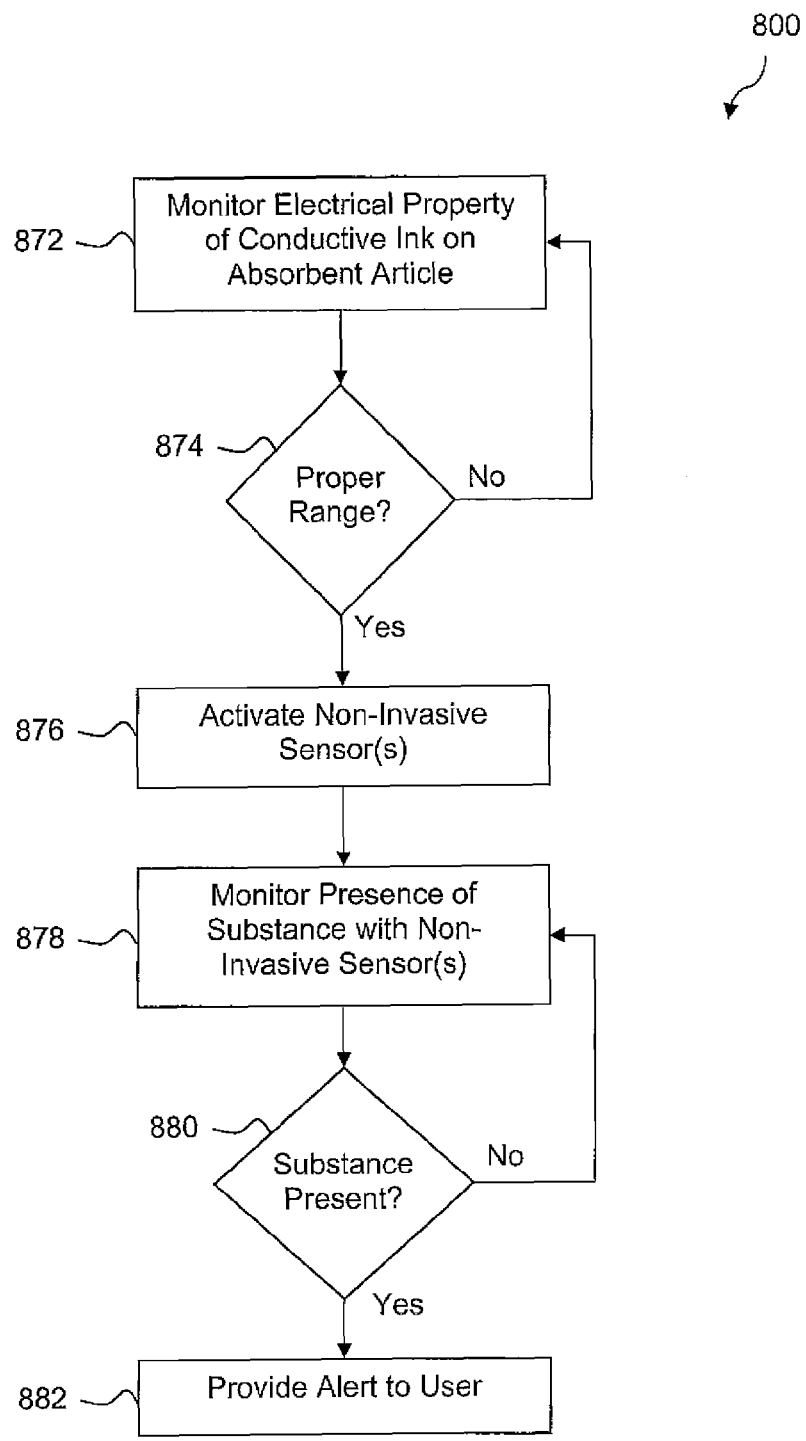
FIG. 12 is a flow diagram of exemplary method steps according to an exemplary embodiment of the present disclosure.

Microcontroller 830 is configured to activate the non-invasive sensors 120 of signaling device 110 if the electrical characteristics detected from the absorbent article falls within a predefined range. FIG. 12 illustrates a flow diagram of an exemplary method 800 performed by microcontroller 830 in activating the signaling device 110. At 872, the microcontroller 830 monitors the electrical characteristics of conductive patterns on the absorbent article by analyzing signals received from electrical property sensor 820. At 874 the microcontroller 830 determines if the electrical characteristics fall within a predefined range. If the electrical characteristics do not fall within the predefined range, the microcontroller 830 never activates the non-invasive sensors 120 of signaling device 110, preventing signaling device 110 from being used on an unauthorized product.

At 876, if the microcontroller 830 determines that the electrical characteristics fall within the predefined range, the microcontroller 830 activates the non-invasive sensors 120. At 878, the microcontroller 830 will monitor the presence of a substance in the absorbent article by analyzing signals received from the non-invasive sensor 120. As indicated at 880, the microcontroller 830 will determine whether a substance is present in the absorbent article based on the signals received from the non-invasive sensors 120. At 884, if a substance is detected, the microcontroller 830 will control alert system 850 to provide a visible and/or audible alert to the user of the absorbent article.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article, comprising:
   a chassis comprising an outer cover having an interior surface and an exterior surface and an absorbent structure positioned adjacent the interior surface of the outer cover;
   a non-invasive signaling device configured to detect the presence of a substance and at least one of a predefined color, a UV pattern, or an infrared light reflectance; and
   at least one attachment zone on the outer cover, the attachment zone configured to receive the non-invasive signaling device, the attachment zone comprising a design scheme printed on the outer cover configured for assisting alignment of the non-invasive signaling device;
   wherein the design scheme comprises at least one identifiable characteristic, the identifiable characteristic comprising a detectable pattern on the attachment zone, the detectable pattern comprising one of a predefined color, a UV pattern, or an infrared light reflectance, wherein the presence of the predefined color, UV pattern, or infrared light reflectance activates the non-invasive signaling device so as to detect the presence of a substance.

2. The absorbent article of claim 1, wherein the detectable pattern comprises a plurality of predefined colors on the absorbent article.

3. The absorbent article of claim 1, wherein the at least one identifiable characteristic comprises the presence of one or more UV patterns arranged in an identifiable pattern, the UV patterns configured to fluoresce when illuminated with electromagnetic energy at a particular frequency.

4. The absorbent article of claim 1, wherein the at least one identifiable characteristic comprises an infrared light reflectance of a material on said absorbent article.

* * * * *